United States Patent [19]

Glass

[11] Patent Number: 4,826,967

[45] Date of Patent: May 2, 1989

[54] PSORALEN-NUCLEOSIDE ADDUCTS AND METHOD FOR THEIR PREPARATION

[75] Inventor: Richard S. Glass, Tucson, Ariz.

[73] Assignee: NAXCOR, Albany, Calif.

[21] Appl. No.: 63,239

[22] Filed: Jun. 16, 1987

[51] Int. Cl.$^4$ ............... C07H 19/067; C07H 19/073; C07H 19/04; C07D 493/00

[52] U.S. Cl. ........................... 536/23; 536/22; 549/282

[58] Field of Search ............... 536/22, 23; 549/282; 204/157.6

[56] References Cited

U.S. PATENT DOCUMENTS 4,599,303  7/1986  Yabusahi et al. ............... 436/501

OTHER PUBLICATIONS

Asker et al., the Chemical Abstracts; col. 520b, vol. 54, 1960.
Shim et al., the Chemical Abstracts, 99:154432y (1983).
Vigny et al., the Chemical Abstracts, 99:206149h (1983).
Cadet et al., the Chemical Abstracts, 106; 152168f (1987).
Jones et al., Nouv. J. Chem. (1985) 9:5–6.
Binkley et al., "Synthetic Organic Photochemistry," W. M. Horspool Ed. Plenum: New York, 1984.

*Primary Examiner*—Johnnie R. Brown
*Assistant Examiner*—Jenny Tou
*Attorney, Agent, or Firm*—Richard L. Neeley

[57] ABSTRACT

A method for the stereoselective snythesis of a cis-syn, furan-side mono-adducted linear furocoumarin:nucleoside adduct, which comprises reacting a linear furocoumarin with a nucleophilic acid to form a 3,4-dihydro-4-substituted linear furocoumarin intermediate, and contacting the intermediate with a nucleoside under photoactivating conditions. The reaction produces a cis-syn, furan-side, mono-adducted 3,4-dihydro-4-substituted linear furocoumarin:nucleoside adduct which can then be deblocked to give the final product under mild conditions.

10 Claims, No Drawings

PSORALEN-NUCLEOSIDE ADDUCTS AND METHOD FOR THEIR PREPARATION

FIELD OF THE INVENTION

This invention relates to photoadducts of furocoumarins (psoralens) with nucleosides and to stereoselective techniques for producing such compounds.

BACKGROUND OF THE INVENTION

Psoralens are linear furocoumarins with the ability to crosslink DNA strands upon photoactivation. A number of different analytical techniques have been devised using this property to form covalent bonds between single-stranded nucleic acid probes containing a base sequence complementary to the base sequence of a nucleic acid target molecule.

A number of synthetic techniques have been devised to prepare nucleosides monoadducted to psoralens for use in these assays. For example, thymidines monoadducted to psoralen, 8-methoxypsoraen, 4,5',8-trimethylpsoralen, and 4'-hydroxymethyl-4,5',8-trimethylpsoralen have been prepared by reaction of these psoralen derivatives with deoxyribonucleic acid followed by enzymatic or chemical hydrolysis of the DNA and chromatographic isolation of the thymidine:psoralen monoadduct. Alternatively, the thymidine:8-methoxypsoralen monoadduct has been prepared from the monomers by irradiating a thin film of the two compounds mixed together. The uridine:4'-hydroxymethyl-4,5',8-trimethylpsoralen monoadduct has been prepared by reacting 4'-hydroxymethyl-4,5',8-trimethylpsoralen with ribonucleic acid followed by the enzymatic or chemical hydrolysis of the RNA and chromatographic isolation of the uridine:4'-hydroxymethyl-4,5',5-trimethylpsoralen monoadduct.

A problem that exists with current photochemical synthesis of adducts is that a mixture of products is produced by current techniques. For example, the photoreaction of 8-methoxypsoralen (1) with 2-deoxythymidine (2) gives a mixture of mono- and di-adducts.

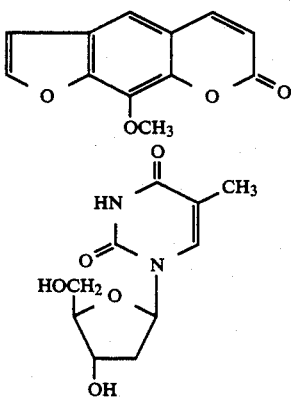

The major monoadduct (with cis-anti stereochemistry) and two minor monoadducts are derived by (2+2) cycloaddition involving the 3,4-double bond of 8-methoxypsoralen (pyrone-side). Two monoadducts, one with cis-syn stereochemistry and the other with trans-stereochemistry, are formed by (2+2) cycloaddition of the 4',5'-double bond (furan-side). The minor cis-syn, furan-side product (3) is the most desirable product for use in preparing photocrosslinkable nucleic acid probes.

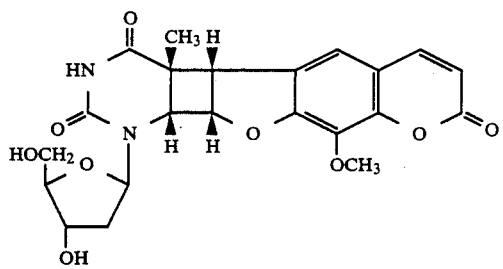

Although separation of the mixture has been achieved, separation is difficult. Accordingly, there remains a need for a synthetic technique which will provide the desired isomer in increased yield and with a simplified course of purification.

RELEVANT LITERATURE

Shim et al., Photochem. Photobiol. (1983) 38: 265–271 describes the photoreaction of 8-methoxypsoralen with 2-deoxythymidine to give a mixture of mono- and di-adducts. U.S. Pat. No. 4,599,303 to Yabasaki et al. summarizes various techniques used to synthesize monoadducts of thymidine with 8-methoxypsoralen and related compounds, and describes techniques for using these monoadducts in the preparation of photocrosslinkable probes.

SUMMARY OF THE INVENTION

A method for the stereoselective synthesis of a cis-syn, furan-side, mono-adducted linear furocoumarin:nucleoside adduct is provided which comprises reacting a linear furocoumarin with a nucleophilic acid to form a 3,4-dehydro-4-substituted linear furocoumarin intermediate and contacting said intermediate with a nucleoside under photoactivating conditions, whereby a cis-syn, furan-side, mono-adducted 3,4-dihydro-4-substituted linear furocoumarin:nucleoside adduct intermediate is formed. The intermediate can be isolated if desired or the adduct intermediate can be hydrolyzed to produce the product linear furocoumarin:nucleoside adduct.

DESCRIPTION OF PREFERRED EMBODIMENTS

A method is provided for preparing cis-syn, furan-side, mono-adducted linear furocoumarin:nucleoside adducts by a stereoselective photosynthesis which avoids the production of 3,4-monoadducts and diadducts. This method is carried out by reacting a linear furocoumarin with a nucelophilic acid to form a 3,4-dihydro-4-substituted linear furocoumarin intermediate prior to carrying out the photoaddition.

A nucleophilic acid, as this term is used in the present invention, is a compound of the formula HX in which H represents an acidic hydrogen and X represents a nucleophilic moiety. The reaction that takes place is a typical 1,4-addition reaction to an $\alpha,\beta$-unsaturated carbonyl group. The final product is a rearrangement product in which H and X add to the $\alpha$ and $\beta$ positions, respectively, of the conjugated carbonyl. This is shown in the following reaction scheme which shows HX adding to psoralen.

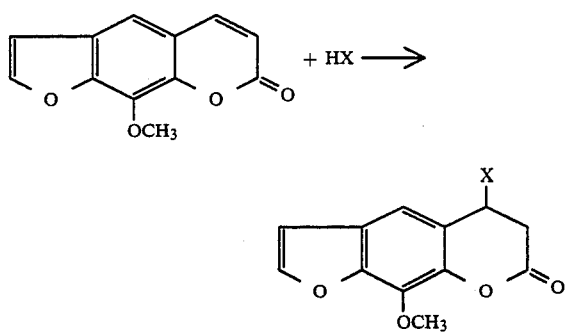

It will be recognized by those skilled in the art of synthetic organic chemistry that the nucleophilic acid need not be presented as such in the reaction. For example, a nucleophile of the formula X⁻ can be used in an initial step followed by acidification of the reaction medium. Accordingly, the term nucleophilic acid, as indicated by the formula HX, represents the molecule being added to the $\alpha,\beta$-double bond and does not necessarily indicate that a molecule of the formula HX is actually presented for reaction with the furocoumarin.

A variety of nucleophiles can be used to block the 3,4-double bond. However, care must be taken to select nucleophiles that can be easily displaced without adversely affecting the remaining structure of the photoadduct, since the blocking group will be removed at a later step. Accordingly, sulfur anions, oxygenated sulfur anions, selenium anions, tertiary amines, oxyanions, fluoride and chloride ions, and cyanide ions have been determined to be appropriate nucleophilic anions. Each of these classes of nucleophiles will be discussed in turn.

Sulfur anions are prepared from hydrogen sulfide and its organic derivatives. Although hydrogen sulfide itself can be added to an $\alpha,\beta$-carbonyl compound, alkane thiols and thiophenols are more reactive and readily usable. The reactivity decreases in the orer thiophenols, primary alkane thiols, secondary alkane thiols, and tertiary alkane thiols. $C_1$-$C_4$ alkane thiols are preferred alkane thiols. Thiophenols can be either thiophenol itself or a substituted thiophenol. Typical aromatic substituents, such as $C_1$-$C_4$ alkyl, halogen, nitro, halo, $C_1$-$C_4$ alkanoyl, $C_1$-$C_4$ alkoxy, amino and alkyl-substituted amino, carboxylate, and carboxylate esters, can be present. Thiophenol and alkyl-substituted thiophenols are preferred.

Addition compounds formed from sulfur anions can be deblocked in a mildly basic solution (e.g. 4% alcoholic potassium hydroxide heated at reflux). Alternatively, the sulfide-blocked compound can be oxidized to a sulfone which can be deblocked under milder conditions (e.g., standing in 4% alcoholic potassium hydroxide at room temperature).

Oxidized sulfur anions include bisulfite anions, sulfinic acid anions, and arene sulfinic acid anions. Preferred alkyl and aromatic substituents are as described above for sulfur anions. The blocked compounds, which are sulfones, are deblocked as described above. Bisulfite addition products can be deblocked by heating under reduced pressure.

Nucleophilic selenium anions can be used in the manner described above for sulfur anions. Deblocking can be easily achieved by oxidation (e.g., with hydrogen peroxide) to the corresponding selenoxide followed by thermal elimination of RSeOH at room temperature or below. See, Paulmier, "Selenium Reagents and Intermediates in Organic Synthesis," Pergamon Press, Oxford (1986); Nicolaou and Petasis, "Selenium in Natural Product Synthesis," CIS, Inc., Philadelphia (1984).

Although primary and secondary amines (including aniline) suffer from the competitive ammonolyses of the lactone ring, tertiary aliphatic amines, pyridine, and related N-aromatics do not have this problem and can be used as blocking groups. For a description of acid-catalyzed addition of pyridine and tertiary anilines to $\alpha,\beta$-unsaturated amides, see Le Berre and Delacroix, *Bull. Soc. Chim. Fr.* (1973) 640–647. Deblocking can be easily achieved with base in analogy with deamination of Mannich base salts. For a review of this chemistry, see Tramontini, *Synthesis* (1973) 745–749. A specific example is set forth in Beke and Szantay, *Chem. Ber.* (1962) 95: 2132.

Oxyanions include wateer, aliphatic alcohols, and phenols. Nucleophilic addition of HO⁻, RO⁻, and ArO⁻ can be prepared in a reaction analogous to the nucleophilic addition of oxyanions to substituted benzylidene Meldrum's acids as described in Bernasconi and Leonarduzzi, *J. Am. Chem. Soc.* (1982) 104: 5133. The alkyl and aromatic groups are as described above. The blocked compounds, stable to irradiation, are easily deblocked on mild acid treatment.

Although addition compounds formed from hydrogen bromide and hydrogen iodide are not likely to be stable to irradiation, the corresponding fluoro and chloro compounds formed by the addition of the corresponding hydrogen halides should be stable. Deblocking can be achieved by treatment with mild base.

Carbanions, other than cyanide, are not likely to be useful. However, the cyanide ion is readily added, and the resulting blocked compound can be deblocked after formation of the photoadduct by mild treatment with base.

Preferred nucleophiles are the cyano group and nucleophilic sulfur and oxygenated sulfur anions, particularly thiophenylate, substituted thiophenylate, and bisulfite ions.

The term linear furocoumarin is used in this specification instead of psoralen, the more common name, in order to avoid confusion between the individual compound known as psoralen and use of the word psoralen as a generic term.

Linear furocoumarins are compounds having the following formula:

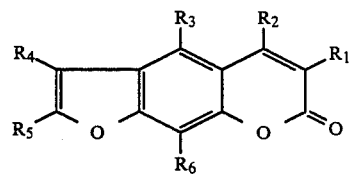

in which each of the groups $R_1$-$R_6$ represents an organic substituent. Typical organic substituents, independently selected for each group, include H, $CH_3$, $CH_2Cl$, $CH_2Br$, $CH_2I$, $CH_2OH$, $CH_2OCH_3$, $CH_2NH_2$, $COOCH_3$, $COOCH_2CH_3$, $NH_2$, $NO_2$, $CF_3$, $CCl_3$, $CH_2CH_3$, $CH(CH_3)_2$, $C(CH_3)_3$, Cl, Br, I, and F. Some naturally occuring and potentially useful psoralens include psoralen itself in which $R_1=R_2=R_3=R_4=R_5=R_6=H$; 8-methoxypsoralen in which $R_1$-$R_5$=H and $R_6$=OCH₃; 5-methoxypsoralen in which all of the substituents are H except $R_3 = OCH_3$; and 4,5',8-trimethylpsoralen in which $R_1 = R_3 R_4 = H$ and $R_2 = R_5 = R_6 = CH = CH_3$. In addition to these compounds, there are 30–40 other naturally occuring psoralens that have been reported.

The nucleosides used in the practice of the present invention are those nucleosides that can readily be incorporated into a DNA or RNA molecule. Both purine and pyrimidine nucleosides can be used. Pyrimidine nucleosides are preferred. Preferred pyrimidines for use in nucleosides are cytosine, uracyl and thymine. The sugar moiety can be either a ribose or a deoxyribose moiety.

Reaction conditions for carrying out the addition reaction between the furocoumarin and the nucleophilic acid are well-known and need not be described in detail. See, for example, Asker et al., *J. Org. Chem.* (1958), 23: 1781; Dodge, *J. Am. Chem. Soc.* (1916) 38: 446; Dodge, ibid. (1930) 52: 1724; Bredt et al., *Justus Liebig's Ann. Chem.* (1896) 293: 338. The reactions are generally carried out in aqueous solutions of the nucleophilic acid optionally containing non-nucleophilic organic solvents, (e.g., N,N-dimethylformamide) to increase solubility of the psoralen. Reactions are generally completed in from a few minutes to a few hours with mild heating (e.g., in a water bath). The intermediates are generally available in nearly quantitative yield and can be isolated by standard techniques, such as cooling aqueous solutions or adding water to solutions containing organic solvents.

The photocycloaddition is carried out by contacting the 3,4-dihydro-4-substituted linear furocoumarin intermediate with a nucleoside under photoactivating conditions. See publications listed under Relevant Literature and the following examples for specific details. The reaction can be carried out in an organic solvent that will not participate in the photocycloaddition reaction, such as methanol and similar alcohol solvents. Reactions can also be carried out by evaporating solutions to provide a film, which is irradiated. Irradiation with a broad spectrum of ultraviolet light is sufficient. Alternatively, an ultraviolet absorbance spectrum of the reaction solution can be taken to determine the optimum wavelength for irradiation. As an initial guide, irradiation at a distance of 1 cm for a total of 10 minutes with a 450 W Hanovia high-pressure mercury arc lamp (or its equivalent) is generally sufficient, although the light flux can be adjusted upward or downward to maximize yield. When irradiating films, it is useful to redissolve the irradiated material, evaporate the solvent, and irradiate again several times. A photosensitizer, such as benzophenone or acetophenone, can be added if desired.

After the photocycloaddition step, the resulting intermediate adduct can be treated to remove the nucleophilic acid blocking agent and produce the normal coumarin unsaturated ring system of the adducted furocoumarin. Typically, deblocking conditions include treatment with dilute alkali bases (either aqueous or alcohol/water solutions) followed by acidification and thermal elimination at room temperature (or above if necesssary). Deblocking conditions will vary depending on the specific blocking agent used. Appropriate deblocking conditions will thus be apparent to those of ordinary skill in the art of organic synthesis. The photoadduct is stable to hydrolysis under many conditions of deblocking and is not affected by this reaction. Even if the lactone ring is hydrolyzed while deblocking with base, it will reform upon acidification.

The reactions set forth above are summarized in the following reaction scheme which shows the blocking of the 3,4-double bond of 8-methoxypsoralen with a variety of nucleophilic acids, formation of a photoadduct of the intermediate with 2-deoxythymidine, and deblocking of the adduct intermediate to give a final product:

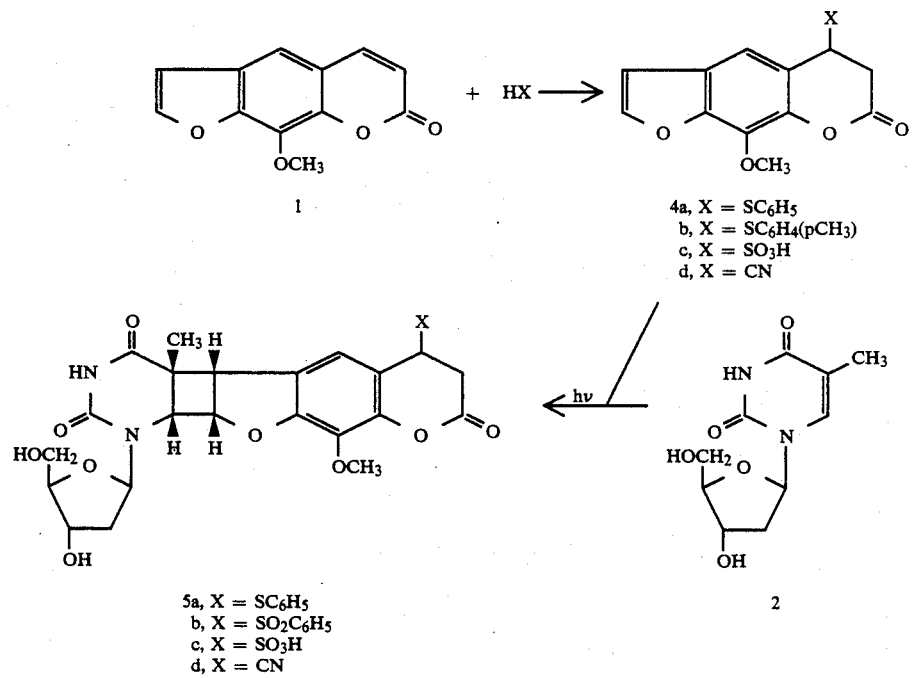

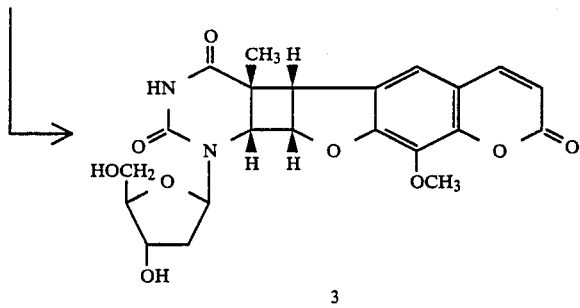

3

The invention now being generally described, the same will be better understood by reference to the following detailed examples which are provided for purposed of illustration only and are not to be considered limiting of the invention unless so specified.

EXAMPLE

Preparation of Bisulfite Adduct 4c of 8-Methoxypsoralen

A mixture of 8-methoxypsoralen (2.16 g, 10.0 mmol) and a 20% aqueous sodium bisulfite solution (15 mL) were shaken and heated on a water bath for 1 hr. A solution was formed which, on cooling, formed a mass of crystals. This mixture was filtered and the precipitate washed with cold water to afford the bisulfate adduct, which gave a negative test with ferric chloride, in nearly quantitative yield.

Preparation of Hydrogen Cyanide Adduct 4d of 8-Methoxypsoralen

A solution of 8-methoxypsoralen (2.16 g, 10.0 mmol), potassium cyanide (1.30 g, 20.0 mmol), and ammonium chloride (0.802 g, 15.0 mmol) in 90% aqueous N,N-dimethylformamide was heated on a water bath for several hours. The solution was cooled, and diluted with water to precipitate adduct 4d. The mixture was filtered and air dried.

Photocycloadditions of Blocked Derivatives 4 with 2-Deoxythymidine

Individual blocked derivatives 4(a-d) and 2-deoxythymidine in a molar ratio of 1:10 were dissolved in methanol. The solution was placed in the well of a photochemical immersion apparatus and evaporated to leave a clear film. The film was placed under a nitrogen atmosphere and irradiated with a 450 W Hanovia high pressure mercury arc lamp through pyrex for 10 minutes at room temperature. The film was redissolved in methanol, the solvent removed, the film again irradiated, and the process repeated several times. Similar experiments were done in the presence of benzophenone or acetophenone (5 molar %) as photosensitizer.

The photoproduct (except for that using 4c) was purified by repeated preparative silica gel TLC eluting with benzene-acetonitrile-ethanol (10:10:1 by volume). This purified material containing photoadducts 5(a-d) was treated as follows.

Conversion of Adduct 5a into Adduct 3

The purified photoproducts containing adduct 5a was stirred and heated at reflux with 4% alcoholic potassium hydroxide (10 mL) for 4 h. The reaction mixture was then allowed to cool to room temperature, poured into ice-cold water, acidified with aqueous hydrochloric acid, and lyophilized. The residue was partially dissolved in acetonitrile-ethanol (10:1). This mixture was chromatographed on preparative silica gel TLC eluting with benzene-acetonitrile-ethanol (10:10:1 by volume) to obtain adduct 3.

Oxidation of Adduct 5a with Hydrogen Peroxide

The purified photoproducts containing adduct 5a was dissolved in glacial acetic acid and aqueous hydrogen peroxide (30%) added. The reaction mixture was stored overnight at room temperature. Concentration of the solution gave a precipitate which was filtered off to give oxidized photoproducts including adduct 5b.

Conversion of Adduct 5b into Adduct 3

The mixture of oxidized photoproducts containing adduct 5b was stirred with 4% alcoholic potassium hydrixide (10 mL) overnight. The reaction mixture was worked up as described for the conversion of adduct 5a into adduct 3 to afford adduct 3.

Conversion of Adduct 5c into Adduct 3

The photoadduct mixture containing 5c was heated at 120° C. under reduced pressure. The residue was dissolved in acetonitrile-ethanol (10:1) and chromatographed on preparative silica gel TLC eluting with benzene-acetonitrile-ethanol (10:10:1 by volume) to obtain adduct 3.

Conversion of Adduct 5d into Adduct 3

The mixture of purified photoproducts containing adduct 5d was stirred and heated at reflux overnight in ethanol saturated with potassium hydroxide. Alternatively, the mixture was dissolved in dimethylsulfoxide containing excess sublimed potassium tert-butoxide and stirred at room temperature for several days. In both cases the base was neutralized, with ice-water cooling, with aqueous hydrochloric acid. The mixture was concentrated to dryness. The residue was dissolved in acetonitrile-ethanol (10:1) and chromatographed on preparative silica gel TLC eluting with benzene-acetonitrile-ethanol (10:10:1 by volume) to obtain adduct 3.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for the stereoselective synthesis of a cis-syn, furan-side, mono-adducted linear furocoumarin:nucleoside adduct, which comprises:

reacting a linear furocoumarin with a nucleophilic acid of formula HX to form a 3,4-dihydro-4-X-substituted linear furocoumarin intermediate;

contacting said intermediate with a nucleoside under photoactivating conditions, whereby a cis-syn, furan-side, mono-adducted 3,4-dihydro-4-X-substituted linear furocoumarin:nucleoside adduct intermediate is formed; and deblocking said adduct intermediate to form said adduct.

2. The method of claim 1, wherein said nucleoside is 2-deoxythymidine, thymidine, 2-deoxyuridine, uridine, 2-deoxycytidine, or cytidine.

3. The method of claim 1, wherein said linear furocoumarin is psoralen, 8-methoxypsoralen, 4,5',8-trimethylpsoralen, or 4'-hydroxymethyl-4,5',8-trimethylpsoralen.

4. The method of claim 1, wherein X is CN, $SC_6H_5$, $SC_6H_4(pCH_3)$, or $SO_3H$.

5. The method of claim 1, wherein HX is a $C_1$–$C_4$ alkanethiol, thiophenol, or a thiophenol substituted with a $C_1$–$C_4$ alkyl, halogen, nito, halo, $C_1$–$C_4$ alkanoyl, $C_1$–$C_4$ alkoxy, amino, alkyl-substituted amino, carboxylate, or carboxylate ester group.

6. The method of claim 5, wherein HX represents thiophenol or an alkyl-substituted thiophenol.

7. The method of claim 5, which further comprises deblocking said adduct intermediate to form said adduct.

8. The method of claim 7, wherein said deblocking comprises heating said adduct intermediate in a basic solution.

9. The method of claim 7, wherein said deblocking comprises oxidizing the sulfur atom of said thiophenol or alkanethiol prior to deblocking.

10. The method of claim 1, wherein said nucleophilic acid is hydrogen bisulfite and said method further comprises deblocking said adduct intermediate to form said adduct by heating said deblocked adduct intermediate under reduced pressure.

* * * * *